(12) United States Patent
Heinz

(10) Patent No.: US 9,121,825 B2
(45) Date of Patent: Sep. 1, 2015

(54) METHODS AND APPARATUSES FOR MEMS BASED RECOVERY OF SEQUENCE VERIFIED DNA

(71) Applicant: CAMBRIAN GENOMICS, INC., San Francisco, CA (US)

(72) Inventor: Austen Heinz, San Francisco, CA (US)

(73) Assignee: Cambrian Genomics, Inc., San Francisco, CA (US)

( * ) Notice: Subject to any disclaimer, the term of this patent is extended or adjusted under 35 U.S.C. 154(b) by 165 days.

(21) Appl. No.: 13/725,300

(22) Filed: Dec. 21, 2012

(65) Prior Publication Data

US 2014/0008223 A1 Jan. 9, 2014

Related U.S. Application Data

(60) Provisional application No. 61/581,015, filed on Dec. 28, 2011.

(51) Int. Cl.
*G01N 27/447* (2006.01)
*B01L 3/00* (2006.01)
*B81B 7/00* (2006.01)
*A61K 48/00* (2006.01)
*G01N 1/00* (2006.01)
*C12Q 1/68* (2006.01)
*A61K 9/00* (2006.01)
*C12N 15/00* (2006.01)

(52) U.S. Cl.
CPC .......... *G01N 27/44791* (2013.01); *A61K 48/00* (2013.01); *B01L 3/50273* (2013.01); *B81B 7/00* (2013.01); *C12Q 1/68* (2013.01); *G01N 1/00* (2013.01); *A61K 9/0097* (2013.01); *C12N 15/00* (2013.01); *G01N 27/447* (2013.01)

(58) Field of Classification Search
None
See application file for complete search history.

(56) References Cited

U.S. PATENT DOCUMENTS

| | | | |
|---|---|---|---|
| 7,705,514 B2 * | 4/2010 | He et al. | 310/309 |
| 2002/0020053 A1 | 2/2002 | Fonash et al. | |
| 2004/0120855 A1 * | 6/2004 | Reichel et al. | 422/67 |
| 2005/0126916 A1 * | 6/2005 | Lockard et al. | 205/50 |
| 2007/0176997 A1 * | 8/2007 | Komatsu et al. | 347/112 |
| 2007/0194225 A1 | 8/2007 | Zorn | |
| 2008/0139409 A1 | 6/2008 | Kim et al. | |

(Continued)

FOREIGN PATENT DOCUMENTS

WO   WO 2013/101773 A1   7/2013

OTHER PUBLICATIONS

Devasia, S. et al., "A Survey of Control Issues in Nanopositioning", IEEE Transactions on Control Systems Technology. Sep. 2007, vol. 15(5), pp. 802-823.

(Continued)

*Primary Examiner* — Robert T Crow
(74) *Attorney, Agent, or Firm* — Kilpatrick Townsend & Stockton LLP

(57) ABSTRACT

A method of retrieving sequence-verified deoxyribonucleic acid (DNA) includes positioning a sequence-verified DNA molecule on a microelectromechanical systems (MEMS) substrate. The MEMS substrate includes an electrostatic actuator and the sequence-verified DNA molecule is positioned adjacent to a moving element. The method also includes applying a voltage between the moving element and a stator to cause a motion of the moving element, thereby ejecting the sequence-verified DNA molecule from the MEMS substrate.

11 Claims, 23 Drawing Sheets

(56) References Cited

U.S. PATENT DOCUMENTS

2009/0092509 A1 4/2009 Barbic et al.
2009/0246080 A1 10/2009 Rivet et al.

OTHER PUBLICATIONS

Goravar, S, et al., "Probabilistic Analysis of a Comb-Drive Actuator", IEEE Sensors Journal. Apr. 2010, vol. 10(4), pp. 877-882.

Notification of Transmittal of the International Search Report and Written Opinion of the International Searching Authority, or the Declaration and International Search Report and Written Opinion of the International Searching Authority for International Application No. PCT/US2012/071474 mailed on May 21, 2013, 13 pages.

* cited by examiner

METHODS AND APPARATUSES FOR MEMS BASED RECOVERY OF SEQUENCE VERIFIED DNA

CROSS-REFERENCES TO RELATED APPLICATIONS

This application claims priority to U.S. Provisional Patent Application No. 61/581,015, filed on Dec. 28, 2011, entitled "METHODS AND APPARATUSES FOR MEMS BASED RECOVERY OF SEQUENCE VERIFIED DNA," the disclosure of which is hereby incorporated by reference in its entirety for all purposes.

BACKGROUND OF THE INVENTION

Currently the limiting factor in synthetic biology is the availability of low cost, accurately synthesized, synthetic DNA. The price of sequence verified DNA has not fallen significantly over last six years in contrast to order of magnitude decreases in the cost of DNA sequencing. Until very recently there were not efficient methods of assembling a large amount of DNA. However, recent work has allowed for the large scale assembly of entire genomes in vivo as well as in vitro assembly using a method known as isothermal or Gibson assembly. Now that methods exist for assembling large amounts of DNA and even transplanting entire chromosomes to change species simply by altering the DNA of the cell, the need for an inexpensive and efficient technique for retrieving sequence-verified DNA is greater than it has ever been.

SUMMARY OF THE INVENTION

The present invention relates generally to the field of DNA synthesis. More specifically, the present invention relates to methods and apparatuses for recovery of sequence verified DNA. Merely by way of example, the invention has been applied to methods and systems for the recovery of DNA using micro-electromechanical system (MEMS) actuators. The methods and techniques can be applied to a variety of DNA sequencing systems.

According to an embodiment of the present invention, a method of retrieving sequence-verified deoxyribonucleic acid (DNA) is provided. The method includes positioning a sequence-verified DNA molecule on a microelectromechanical systems (MEMS) substrate. The MEMS substrate includes an electrostatic actuator and the sequence-verified DNA molecule is positioned adjacent to a moving element. The method also includes applying a voltage between the moving element and a stator to cause a motion of the moving element, thereby ejecting the sequence-verified DNA molecule from the MEMS substrate.

According to another embodiment of the present invention, a method of retrieving sequence-verified DNA is provided. The method includes positioning a sequence-verified DNA molecule on a microelectromechanical systems (MEMS) substrate. The MEMS substrate includes a magnetic actuator having a movable magnetic arm and the sequence-verified DNA molecule is positioned adjacent to the movable magnetic arm. The method also includes applying a magnetic field in a space surrounding the movable magnetic arm to cause a motion of the movable magnetic arm, thereby ejecting the sequence-verified DNA molecule from the MEMS substrate.

According to an alternative embodiment of the present invention, a method of retrieving sequence-verified DNA is provided. The method includes positioning a sequence-verified DNA molecule on a microelectromechanical systems (MEMS) substrate. The MEMS substrate includes a piezoelectric actuator having at least one movable part. The sequence-verified DNA molecule is positioned adjacent to the movable part of piezoelectric actuator. The method also includes applying an electric filed in the piezoelectric actuator to cause a motion of the movable part, thereby ejecting the sequence-verified DNA molecule from the MEMS substrate.

According to another alternative embodiment of the present invention, a method of retrieving sequence-verified DNA is provided. The method includes positioning a sequence-verified DNA molecule on a microelectromechanical systems (MEMS) substrate. The sequence-verified DNA molecule can be in an aqueous environment or a dry environment. The MEMS substrate includes a thermal actuator having a bimetallic cantilever arm. The sequence-verified DNA molecule is positioned adjacent to a tip of the bimetallic cantilever arm. The method also includes generating a heat in the bimetallic cantilever arm to cause a deflective motion of the bimetallic cantilever arm, thereby ejecting the sequence-verified DNA molecule from the MEMS substrate.

As an example, positioning the sequence-verified DNA molecule can include forming the sequence-verified DNA molecule on the MEMS substrate or transferring the sequence-verified DNA molecule onto the MEMS substrate. In one embodiment, the bimetallic cantilever arm includes two strips of materials of differing thermal coefficients bonded together, and the heat is generated by applying a current through one of the two strips of materials. The MEMS substrate can further include a movable U-shaped electrode surrounding the bimetallic cantilever arm. The movable U-shaped electrode and the bimetallic cantilever arm form an electrostatic comb-drive. In this example, the method also includes concurrent to generating a heat, applying a voltage between the movable U-shaped electrode and the bimetallic cantilever arm to activate the electrostatic comb-drive.

According to a specific embodiment of the present invention, a method of retrieving sequence-verified deoxyribonucleic acid (DNA) is provided. The method includes positioning a sequence-verified DNA molecule on an jet-based system. The jet-based system comprises an orifice and the sequence-verified DNA molecule is positioned adjacent to the orifice. The method also includes causing a fluid to pass through the orifice, thereby ejecting the sequence-verified DNA molecule from the jet-based system. The jet-based system can include a thermal jet system or a piezoelectric jet system.

Numerous benefits are achieved by way of the present invention over conventional techniques. For example, embodiments of the present invention provide a method for recovering DNA at scale by combining massively parallel synthesis and sequencing. Sequencing not only clones, isolates, and allows the user to know the location of the sequence for recovery—it also allows the user to know if the sequence is correct. By sequencing prior to synthesis the number of DNA strands can be assembled increases because there is a much greater likelihood of having an assembled sequence that is error free. When using DNA produced on columns correct sequences are mixed with incorrect sequence, exponentially increasing the likelihood of the assembled sequence having an error with each additional oligo included in the assembly. Using MEMS based capture allows many more pieces to be assembled without error. These and other embodiments of the invention along with many of its advantages and features are described in more detail in conjunction with the text below and attached figures.

BRIEF DESCRIPTION OF THE DRAWINGS

FIGS. 14A-14 F are simplified schematic diagrams illustrating a DNA ejection device using a combination of a lateral electrostatic comb-drive actuator and a thermal bimetallic actuator;

DETAILED DESCRIPTION OF SPECIFIC EMBODIMENTS

Figure 1:
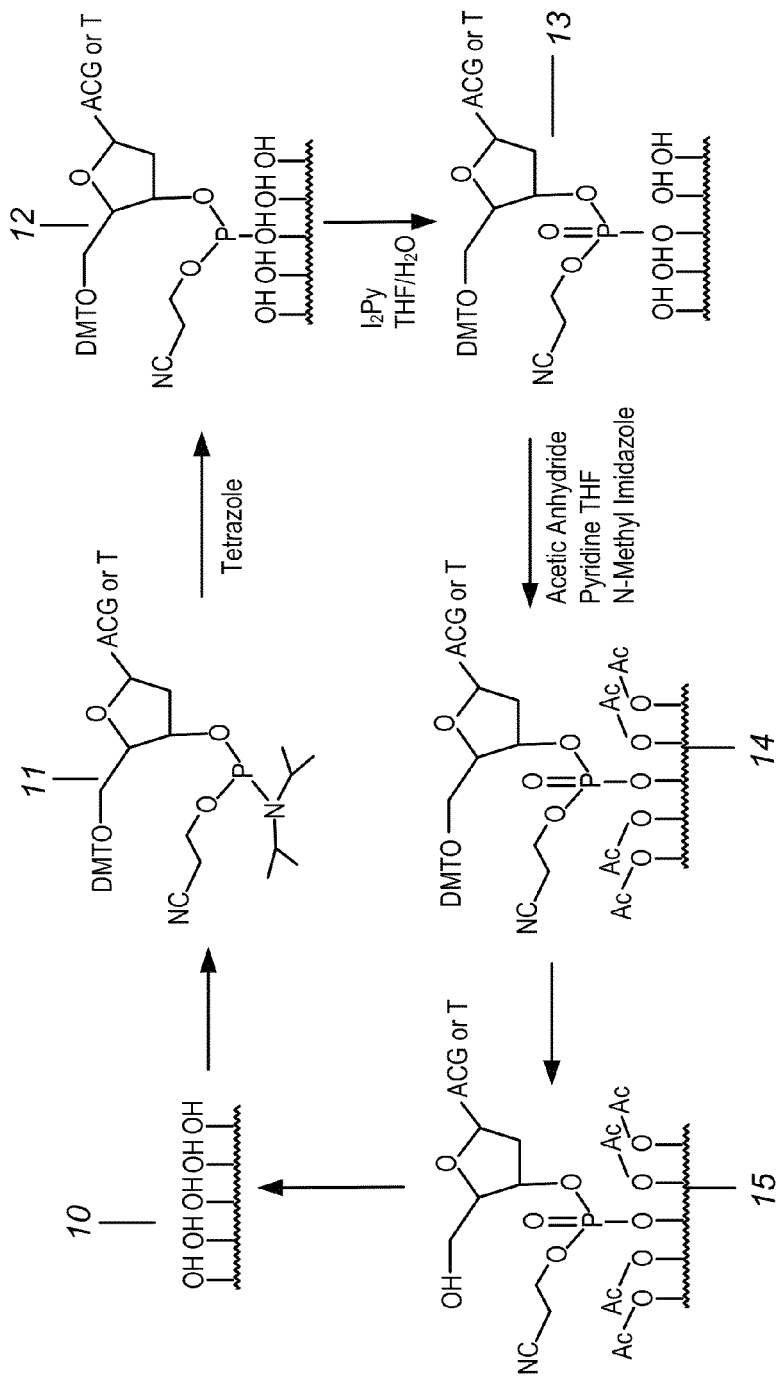
FIG. 1 is a simplified schematic diagram illustrating a method of DNA synthesis using acid based deprotection of the DMT group.

The present invention relates generally to the field of synthetic biology, artificial DNA synthesis, and DNA sequencing. More specifically, the present invention relates to methods and apparatuses for the fabrication of genes, gene circuits, small mitochondrial chromosomes, and large bacterial chromosomes. The present invention is also relevant to whole genome modification such as codon optimization or alternate codon schemes for artificial amino acids or any other project related to large scale rewriting.

Currently the limiting factor in synthetic biology is the availability of low cost error free synthetic DNA. The price of DNA for the last six years has remained around one dollar per base pair for perfect DNA. Until very recently there were not efficient methods of assembling a large amount of DNA. However, work by Gibson et al has allowed for the large scale assembly of entire genomes in vivo (in yeast) as well as in vitro assembly using a method known as isothermal or Gibson assembly. Now that methods exist for assembling large amounts of DNA and even transplanting entire chromosomes to change species simply by altering the DNA of the cell, the need for inexpensive DNA is greater than it has ever been.

According to an embodiment of the present invention, methods and systems are provided that through Sanger sequencing and image processing of both the 454 well image files along with image processing of the physical chip can be used to align sequence data onto physical wells in a realistically feasible manner. One advantage of the methods disclosed herein is that these methods are contact free. Therefore it is not necessary to replace tips after each picking event, as may be used in a mechanical picking apparatus. The problem of cross contamination is also circumvented. These methods and systems are provide practical means for large-scale retrieval of sequence-verified DNA.

Here we describe general systems along with specific detailed examples for an existing sequencing technology. The following description and drawings are illustrative of the invention and are not to be thought of as limiting the invention. Numerous specific details are described to provide a thorough understanding of the present invention. However, in certain instances, well-known or conventional details are not described in order to not unnecessarily obscure the present invention in detail.

Several issues arise when attempting to build a MEMS based DNA retrieval system. The first is whether the actual sequencing should be done on the MEMS device or if the sequencing should be done off the device. If done on the device then the surface chemistry of the MEMS device must be modified to bind the clonal DNA in a patterned manner. Furthermore the MEMS device must be able to withstand exposure to DNA sequencing reagents. This requires proper insulation such as parylene. Potentially a more simple approach is to use a patterned flow cell and then transfer the sequenced clonal DNA onto a MEMS device for release. The ejection mechanisms described here may be used before or after transfer. Another important distinction is whether the ejection is done dry or in an aqueous environment, such as might be the case when using an inkjet type ejection approach. The inkjet or bubble jet approach is attractive because it is non-contact and reliable, and doesn't have the typical sort of cross contamination drawbacks that other liquid based retrieval mechanisms may be faced with.

Although not shown, all clonal DNA to be released can have a sacrificial or ejection layer underneath it to protect it from direct contact with the ejection apparatus. Another major issue is stiction which is a failure caused by excessive adhesive force which in this case is between the ejected DNA and accompanying substrate FIG. 1 is a simplified schematic diagram illustrating a method of DNA synthesis using acid based deprotection of the DMT group. The DNA synthesis process uses a hydroxyl linker surface and the addition of a nucleoside phosphoramidite 11. Tetrazole is added, allowing the coupling reaction to occur between the nucleoside phosphoramidite and the scaffold 12. To complete the coupling reaction THF/$H_2O$ are added 13 to stabilize the phosphite triester internucleosidic linkage. Next a capping reaction is performed by the addition of acetic anhydride, pyridine THF, and N-Methyl Imidazole. After the completion of the coupling reaction, a small percentage of the solid support-bound 5'-OH groups remain unreacted and need to be blocked from further chain elongation to prevent the formation of oligonucleotides with an internal base deletion 14. Afterwards the next deprotection step is performed in which an acid is used to remove the DMT group, thereby starting the process over 15.

Figure 2:
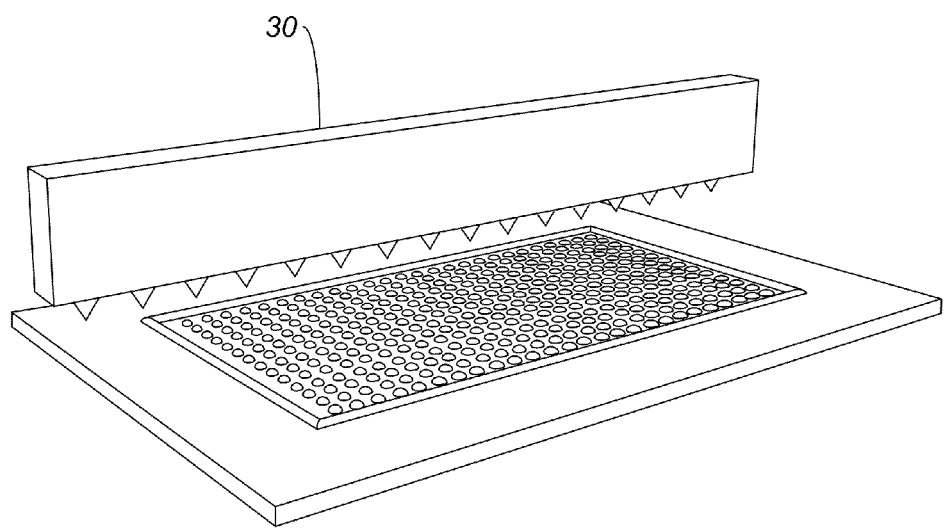
FIG. 2 is a simplified schematic diagram illustrating an inkjet based oligosynthesis setup.

FIG. 2 is a simplified schematic diagram illustrating an inkjet based oligosynthesis setup. A inkjet printer head 30 is used for standard phosphoramidite chemistry. Inkjet fabricated oligos are desirable because of the low error rates, which allow for the fabrication of long sequences that greater than 150 bp.

Figure 3:
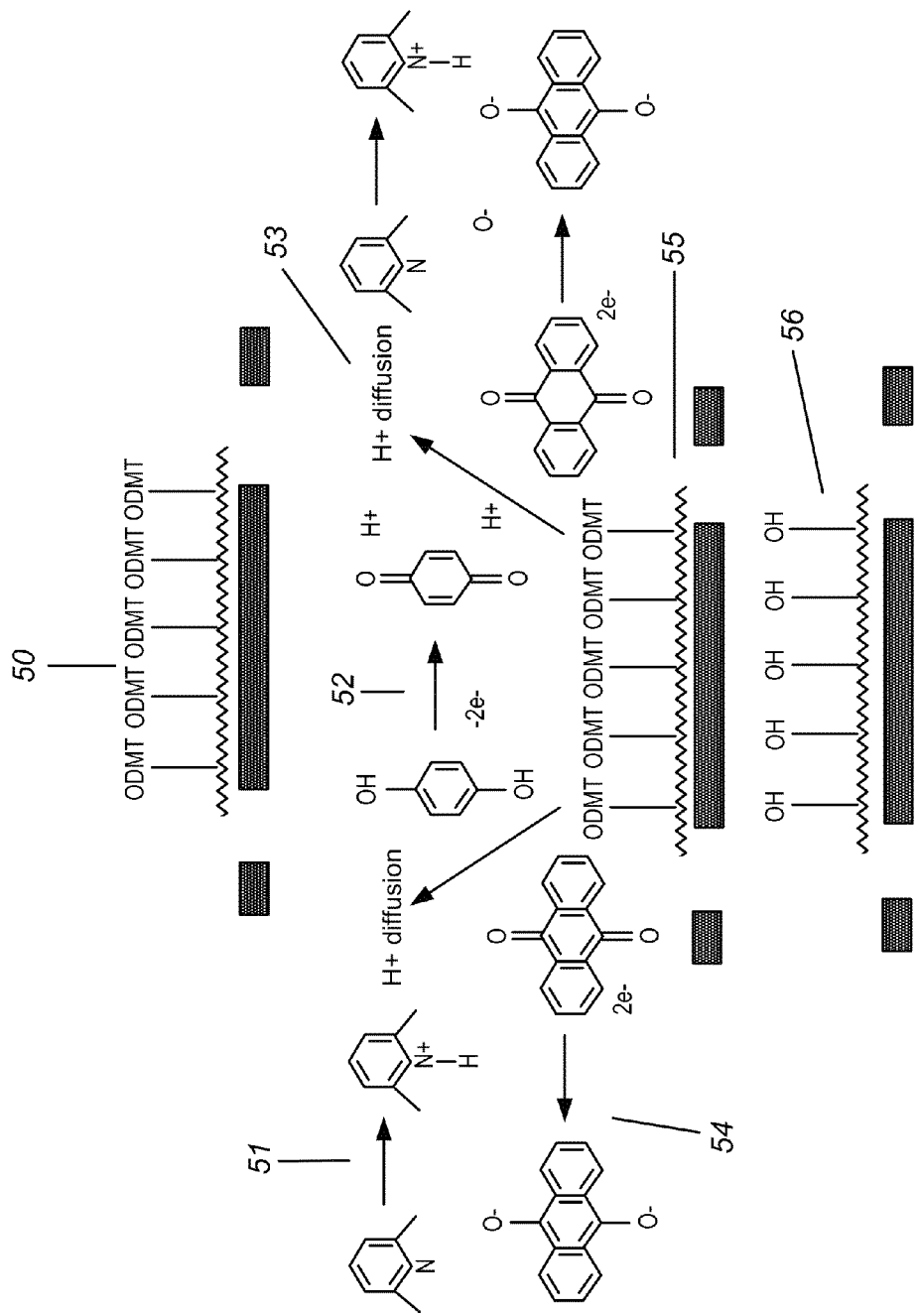
FIG. 3 is a simplified schematic diagram illustrating an electrode based mechanism for DNA synthesis.

FIG. 3 is a simplified schematic diagram illustrating an electrode based mechanism for DNA synthesis. Circular platinum anodes approximately 100 um are surrounded by cathodes. In the region in immediate proximity to the anode an acidic environment is generated in response to a voltage set via connection to an external PC. Diphenylhydrazine 52 is used as the electrogenerated acid. Acid diffuses outside the electrode region which can result in cross-contamination. To contain this acid within isolated regions a base is included in the medium 51. The surrounding cathode activates a neutralizing base 53, which does not effect the DMT protection groups. The electrode is shown before 50, during 51, and after activation 52.

Figure 4:
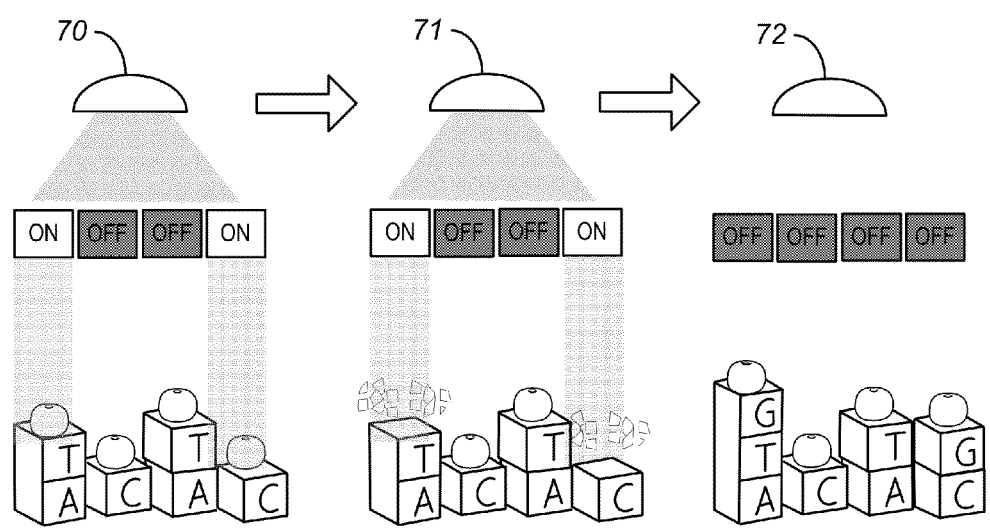
FIG. 4 is a simplified schematic diagram illustrating an iterative photochemical process for DNA synthesis.

FIG. 4 is a simplified schematic diagram illustrating an iterative photochemical process for DNA synthesis. This illustration is designed to represent both NPPOC and standard phosphoramidite chemistry in which a photogenerated acid (PGA) such as $CH_2Cl_2$ is used for deprotection. When the oligos are hit with light 70 the protective group is removed 71 and next dNTP can be added (in this case G) 72. As with all synthesis approaches, a flow cell is necessary. There are several options here ranging from building customized individually automated valves to simply using a modified DNA synthesizer such as the ABI 391 as in the microfluidic array synthesizer (MarS) design or a Expedite 8909 DNA synthesizer in the photogenerated acid approach currently used by LC Sciences.

Figure 5:
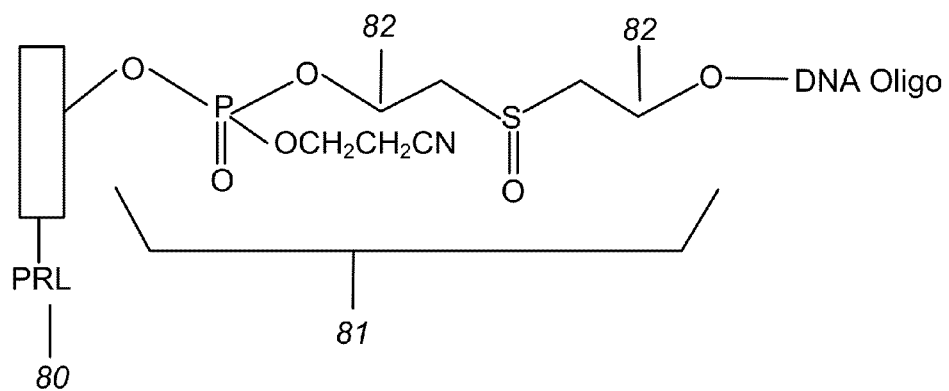
FIG. 5 is a simplified schematic diagram illustrating the release of a DNA molecule in a electrode based DNA synthesis scheme.

FIG. 5 is a simplified schematic diagram illustrating the release of a DNA molecule in a electrode based DNA synthesis scheme. The DNA is attached to a semiconductor porous reaction layer PRL 80 which provides a solid support for attachment, similar to controlled pore glass CPG used in the column of a commercial synthesizer. Base cleavable linkers can be used to release the DNA from the substrate so that the DNA can be recovered. Unlike PCR based recovery shown in the next figure cleaving the DNA from the substrate and directly sequencing does not introduce errors and can result in more stable stoichiometry during sample prep and sequencing. 81 shows the linker unit produced by a chemical phosphoralation reagent.

Figure 6:
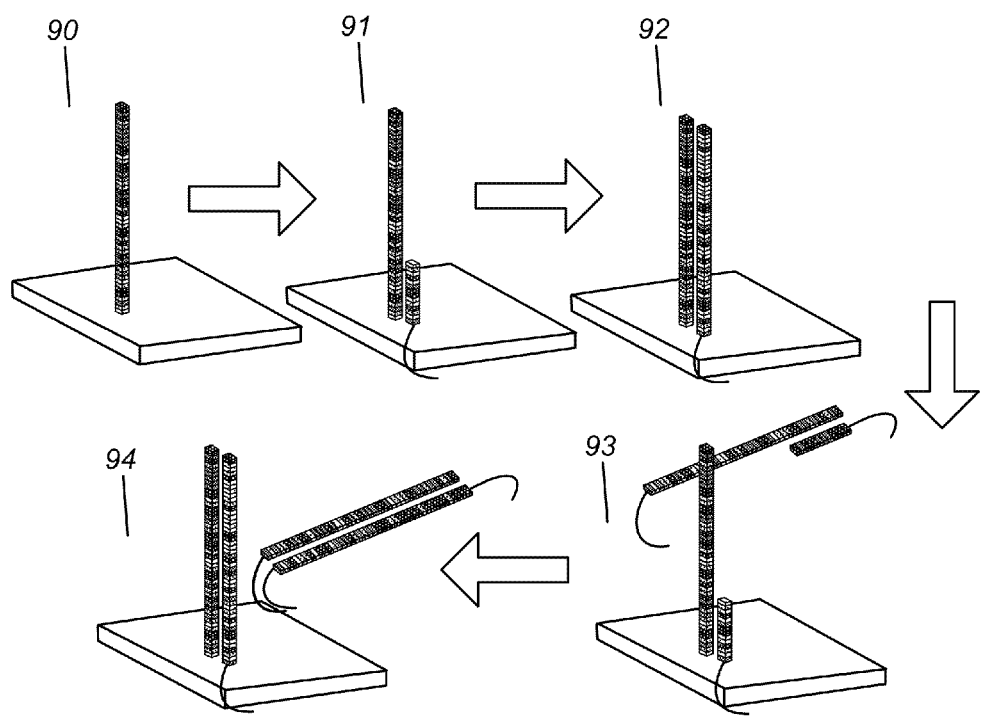
FIG. 6 is a simplified schematic diagram illustrating the amplification of substrate bound oligos using polymerase chain reaction (PCR)

FIG. 6 is a simplified schematic diagram illustrating the amplification of substrate bound oligos using polymerase chain reaction (PCR). FIG. 6 shows PCR amplification of substrate bound i.e. microarray DNA prior to primer binding 90, after primer binding 91, after extension 92, after extension of dehybidization and primer binding to both strands 93, and after extension of both strands 94. This approach has been used previously to provide DNA for subsequent assembly. Amplification can be done from both microarray manufacturers such as Agilent as shown and from free floating oligos that are provided from LC sciences.

Figure 7:
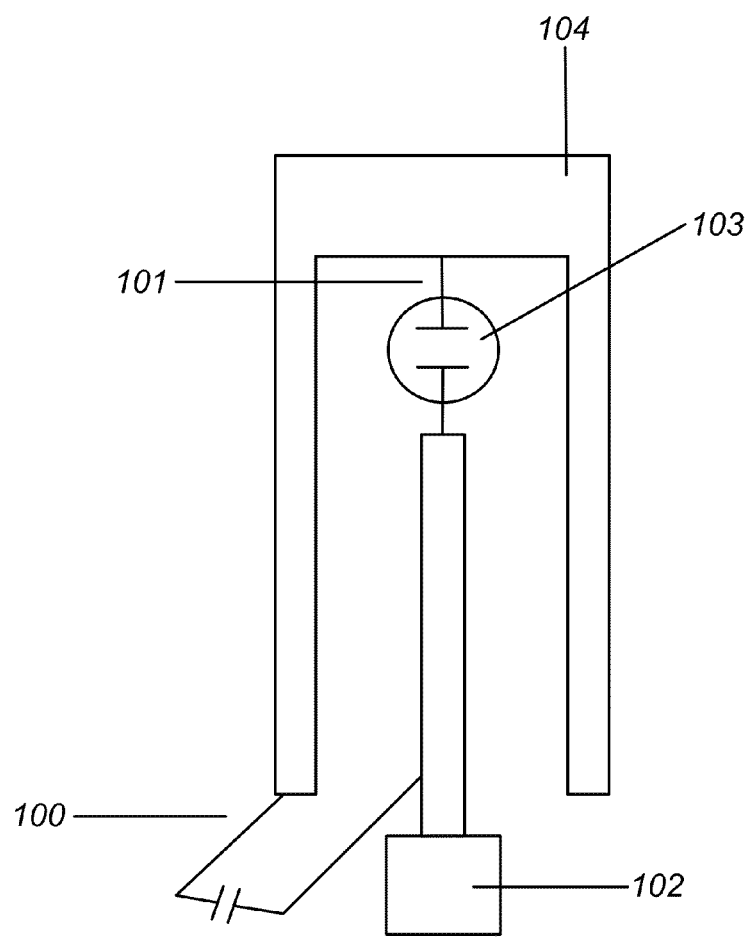
FIG. 7 is a simplified schematic diagram illustrating lateral electrostatic comb-drive DNA ejection device.

FIG. 7 is a simplified schematic diagram illustrating a lateral electrostatic comb-drive DNA ejection device. Electrostatics drives operate on the principle of electric charge. These microscale devices have high surface area to volume ratios. As with other MEMS based DNA systems described here, sequencing can be done on the MEMS device or transferred to the MEMS device after sequencing. The lateral comb drive DNA release device works on the principles of electrostatics. In the comb drive a central comb has one charge along with two outer combs that have opposite charge. 101 is the fringe capacitance between the end of the moving beam 104 and the stator comb 102 (highly non-linear). 100 is the normal capacitance between beams. Not shown is a mechanical connection between the combs with spring constant $K_m$. When the device is actuated substrate bound DNA 103 located between the combs is ejected.

Referring again to FIG. 7, the DNA 103 can be one or several types including a cluster, a polony, or a rolony. In operation, a bias is placed across the stator comb 102 and the moving beam 104, which ejects the DNA as contact is made.

Figure 8:
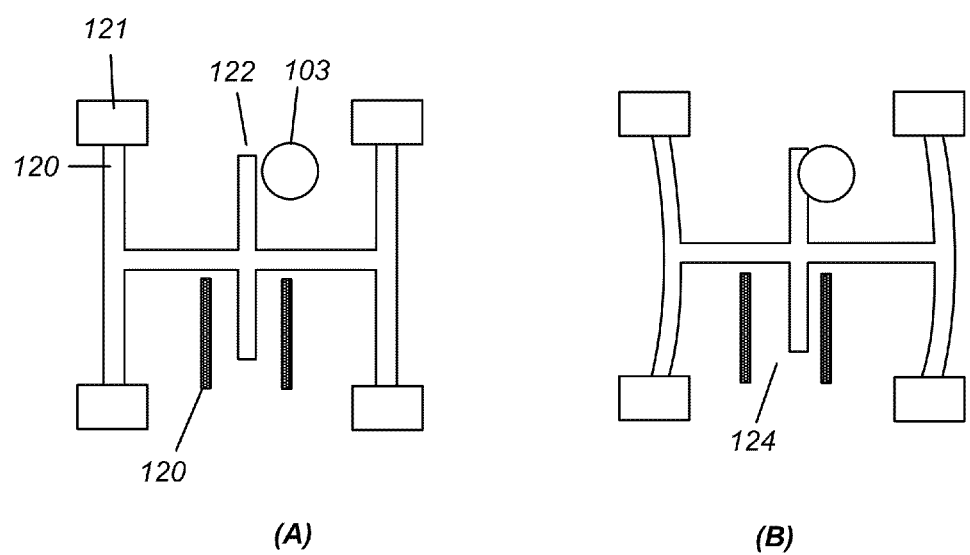
FIGS. 8A and 8B are simplified schematic diagrams illustrating a transverse electrostatic comb-drive DNA ejection device.

FIGS. 8A and 8B are simplified schematic diagrams illustrating a transverse electrostatic comb-drive DNA ejection device. Unlike the lateral comb drive, in the transverse comb drive, both combs 121 are anchored. The dark electrodes are the stators 120. Initially, the finger 122 is positioned at a first position, for example, equidistant between stators as illustrated in FIG. 8A. As illustrated in FIG. 8B, the finger 122 is movable, due to the bending of the flexible beams. The displacement of the finger to the right (to position 124 illustrated in FIG. 8B) causes the DNA bound carrier 103 to be ejected. In some implementations, in addition to the motion illustrated in FIGS. 8A-8B, vibrational motion of the finger 122 can be used to overcome stiction between the DNA 103 and the finger 122. Moreover, heat can be added to the system to stimulate release/ejection in some embodiments. One of ordinary skill in the art would recognize many variations, modifications, and alternatives.

Figure 9:
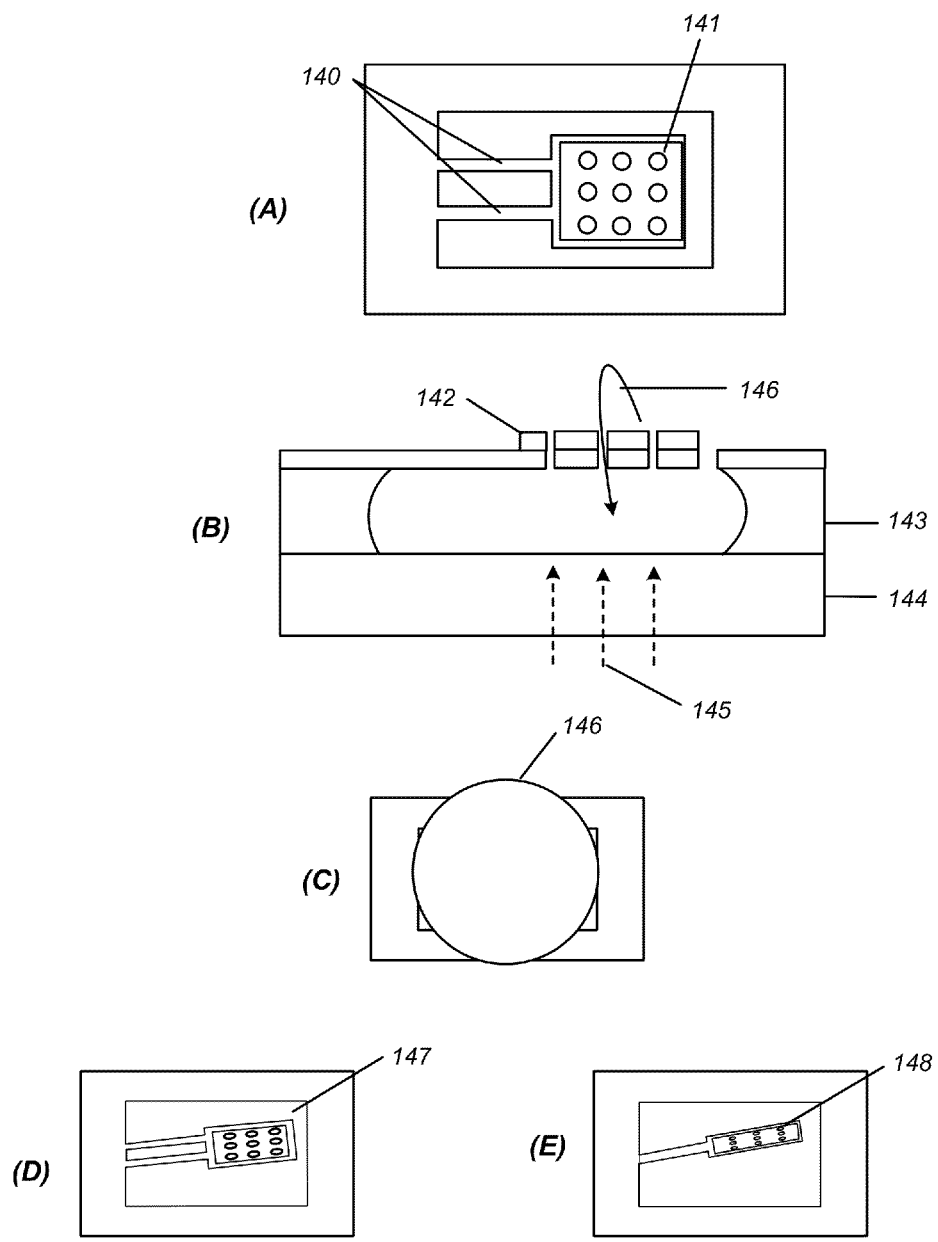
FIGS. 9A-9E are a simplified schematic diagrams illustrating a magnetic torsion-type DNA ejection device.

FIGS. 9A-9E are a simplified schematic diagrams illustrating a magnetic torsion-type DNA ejection device. In this device a permalloy plate 142 is rotated through the application of a magnetic field 145. The structure 141 and the support beams 140 are made of polycrystalline thin film, etched in phosphosilicate glass (PSG) 143 on a silicon substrate 144. The carrier bound DNA before and after ejection 147, 148 from the torsion based magnetic ejection device. As illustrated in FIG. 9B, structure 141 twists tortionally as illustrated by rotation 146 in order to eject the DNA. FIGS. 9D and 9E illustrate rotation of the device as the torsion angle increases. In some embodiments, the DNA is sequenced on the device 141. In other embodiments, the DNA is sequenced separately (e.g., on a glass substrate or other suitable patterned flow cell) and then transferred to device 141. One of ordinary skill in the art would recognize many variations, modifications, and alternatives.

Figure 10:
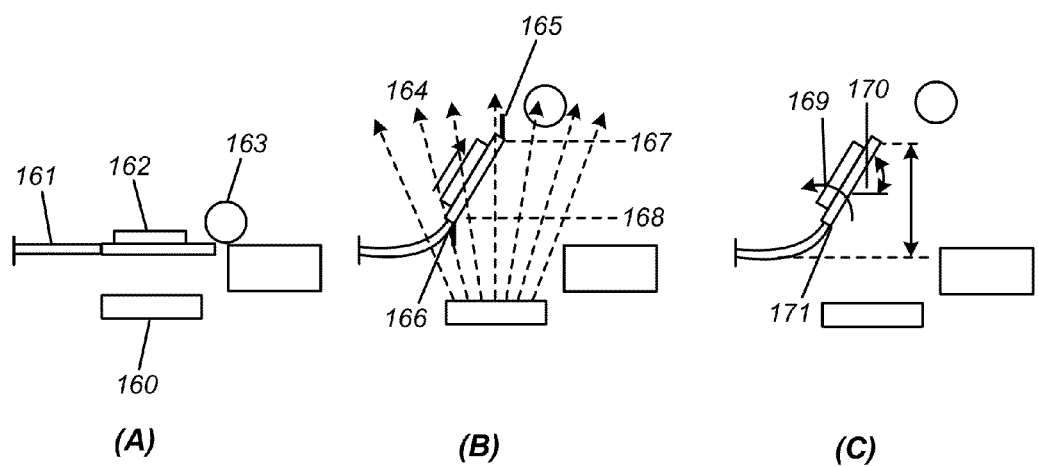
FIGS. 10A-10C are simplified schematic diagrams illustrating a magnetic cantilever DNA ejection device.

FIGS. 10A-10C are simplified schematic diagrams illustrating a magnetic cantilever DNA ejection device biased using an external electromagnet. Due to the force on the permalloy 162 the arm 161 bends in the presence of the applied magnetic field 164. This leads to the ejection of the carrier bound DNA 163. $F_1$ 165 and $F_2$ 166 are the forces applied on the upper and lower portions of the plate. A simplified force diagram is shown in the third image where 169 represents the torque and the combined force acting on the free ends. 170 shows the angle of rotation caused by the magnetic deflection. As the magnetic field is applied from magnet 160, the cantilever arm bends away from the magnet as illustrated in FIG. 10B, resulting in ejection of the DNA 163 from the cantilever arm.

Figure 11:
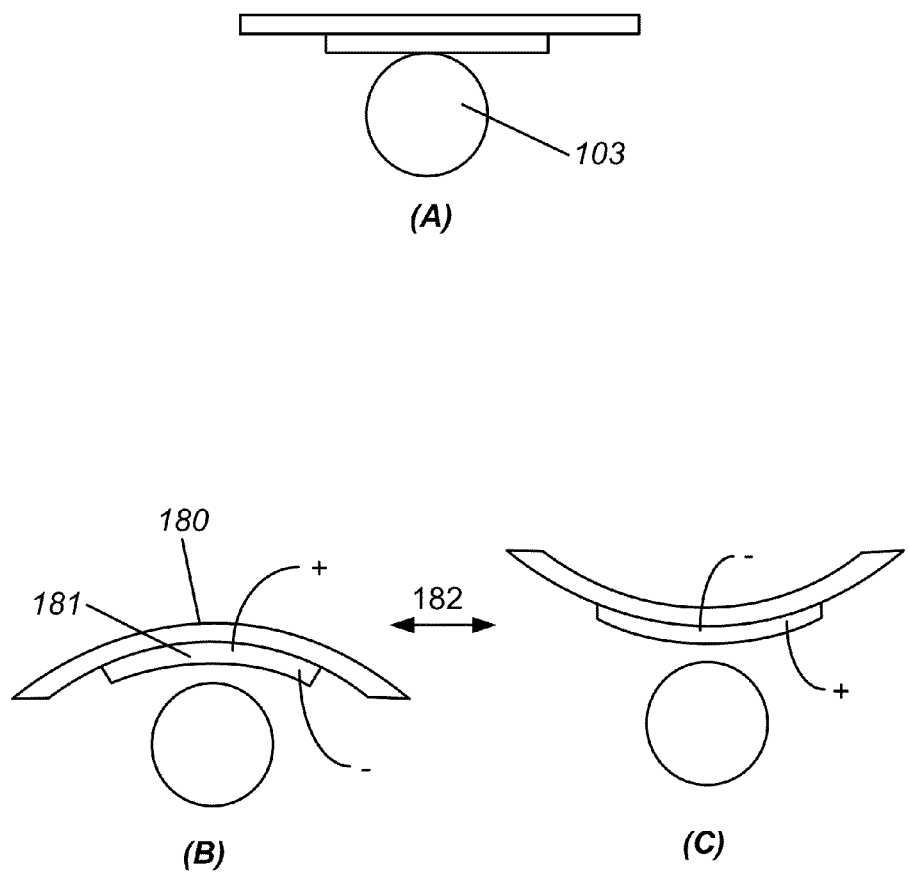
FIGS. 11A-11C are simplified schematic diagrams illustrating a piezoelectric DNA ejection device.
Figure 12:
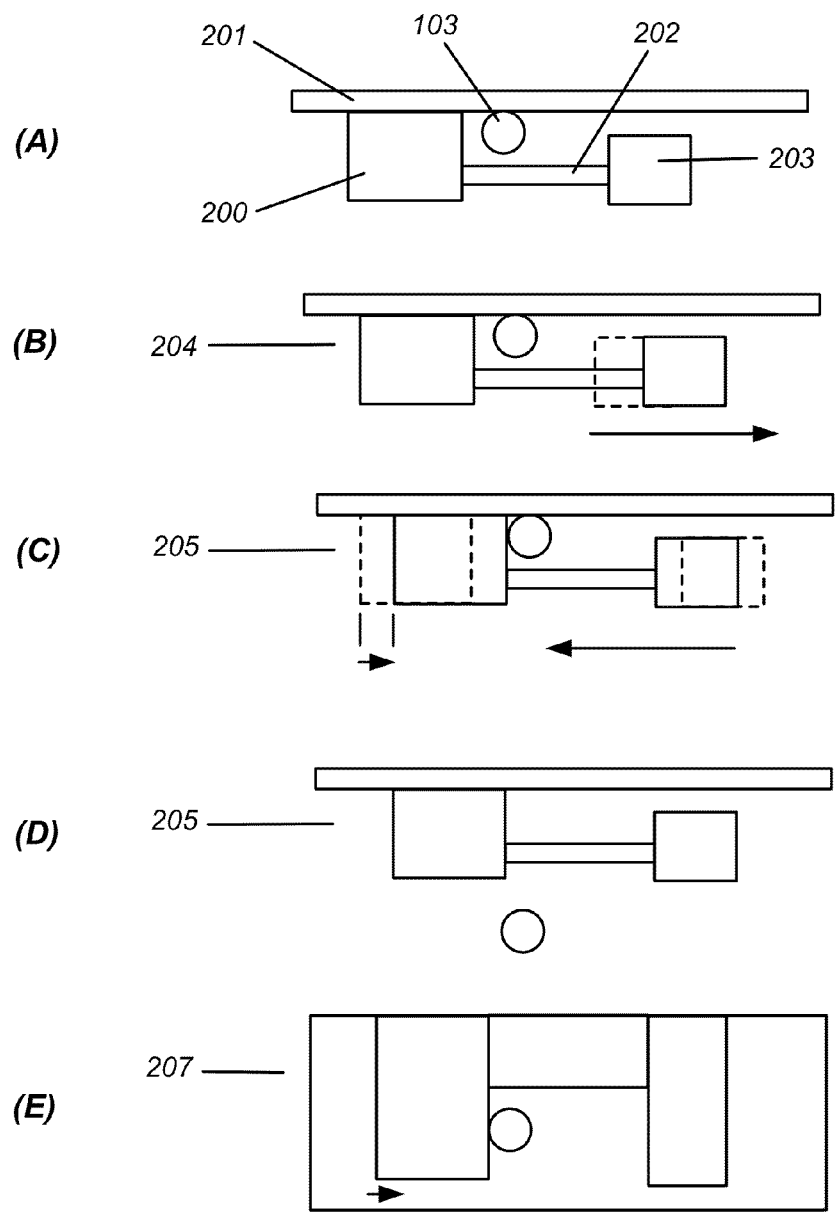
FIGS. 12A-12E are simplified schematic diagrams illustrating a slip-stick piezoelectric DNA ejection device.
Figure 13:
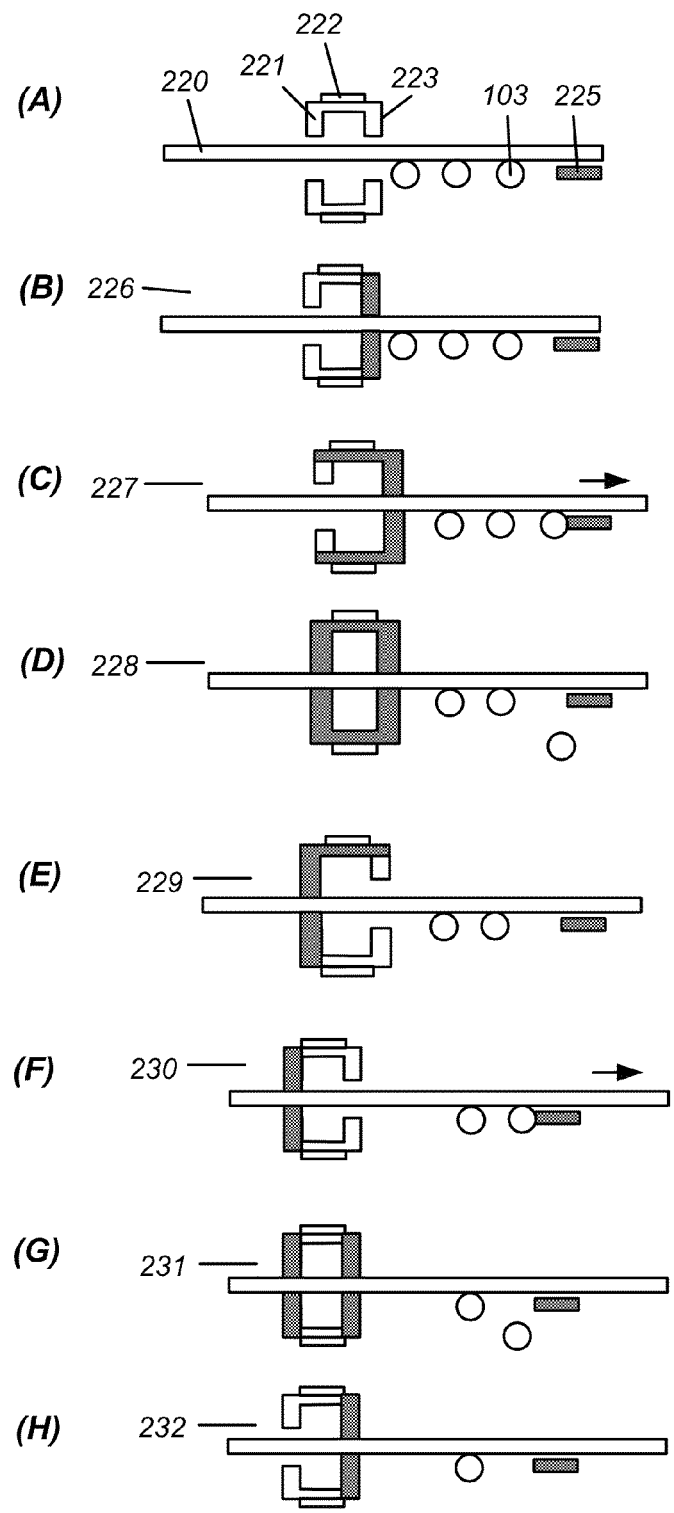
FIGS. 13A-13H are simplified schematic diagrams illustrating a inchworm piezoelectric DNA ejection device.

FIGS. 11A-11C are simplified schematic diagrams illustrating a piezoelectric DNA ejection device. Certain crystals or ceramics exhibit a property whereby they generate an electric field in the presence of a mechanical force. These materials also undergo a reverse piezoelectric effect whereby they generate internal mechanical strain resulting from an applied electric field. It is this effect that is used for DNA ejection. FIGS. 11A-11C show a piezoelectric plate with carrier bound DNA attached and subsequent release. The figure shows the change in polarization that occurs with mechanical deformation. Suitable materials include natural materials such as Berlinite ($AlPO_4$), quartz, and Topaz and man-made crystals such as Gallium orthophosphate ($GaPO_4$), Langasite($La_3Ga_5SiO_{14}$). Suitable manmade ceramics include Barium titanate ($BaTiO_3$), Lead titanate ($PbTiO_3$), Lead zirconate titanate, Lithium niobate ($LiNbO_3$), Lithium tantalite ($LiTaO_3$), Sodium tungstate ($Na_2WO_3$). Some polymers such as polyvinylidene fluoride (PVDF) may also be suitable. The figure shows the piezo material onto which the DNA entity is bound 181 as well as the flexible backing material. The change in polarization in the material upon actuation is shown 182. This can be used for concave or convex ejection. The DNA 103 is attached to the piezoelectric structure. Application of a bias will result in change of the curvature of surfaces of 180 and 181, resulting in ejection of the DNA 103.

FIGS. 12A-12E are simplified schematic diagrams illustrating a slip-stick piezoelectric DNA ejection device. Stick slip works on the principle that the kinetic friction coefficient is lower than the static friction coefficient. In the piezo slip stick the piezo is located between the base and actuator undergoes a slow extension followed by a rapid contraction. 200 is the base plate, 201 the base, 202 the piezo and 203 the actuator. In the first step 204 the piezo extends propelling the actuator forward eventually the force of the piezo is insufficient to overcome the dynamic friction 205. However the base is pulled forward and the piezo is ready to be actuated again. In the process of being pulled forward the base ejects the carrier bound DNA 206. A top view is also shown 207.

FIGS. 13A-13H are simplified schematic diagrams illustrating an inchworm piezoelectric DNA ejection device. The device uses piezoelectric actuators to move the shaft 220. A lateral piezo 222 is used to move either the forward 223 or aft 221 clutching piezos. In order to move the shaft forward the forward clutching piezos expand so contact is made with the shaft and lateral actuators expand 227. Next the aft clutch piezos extend 228. Next the forward clutch piezos retract 229 and the lateral clutch piezos retract again pushing the track forward ejecting the sequencing scaffold as it comes into contact with the ejection stator 225. The process can be repeated to eject multiple sequencing scaffolds from the same ejector track 231 and 232. Thus, operation in a manner similar to a worm motor is provided as sequential actuation of the vertical/horizontal/vertical piezos pushes shaft 220 to the right, ejecting DNA 103 as they make contact with stator 225 as the shaft 220 slides past the stator.

Figure 14:
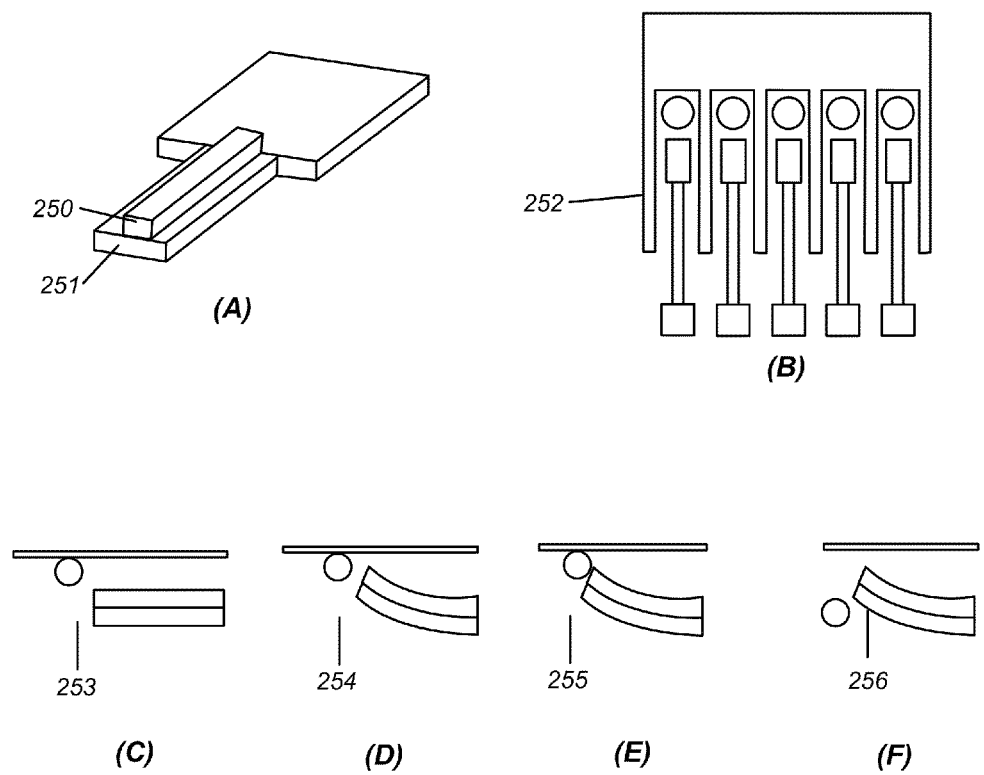
Figure 15:
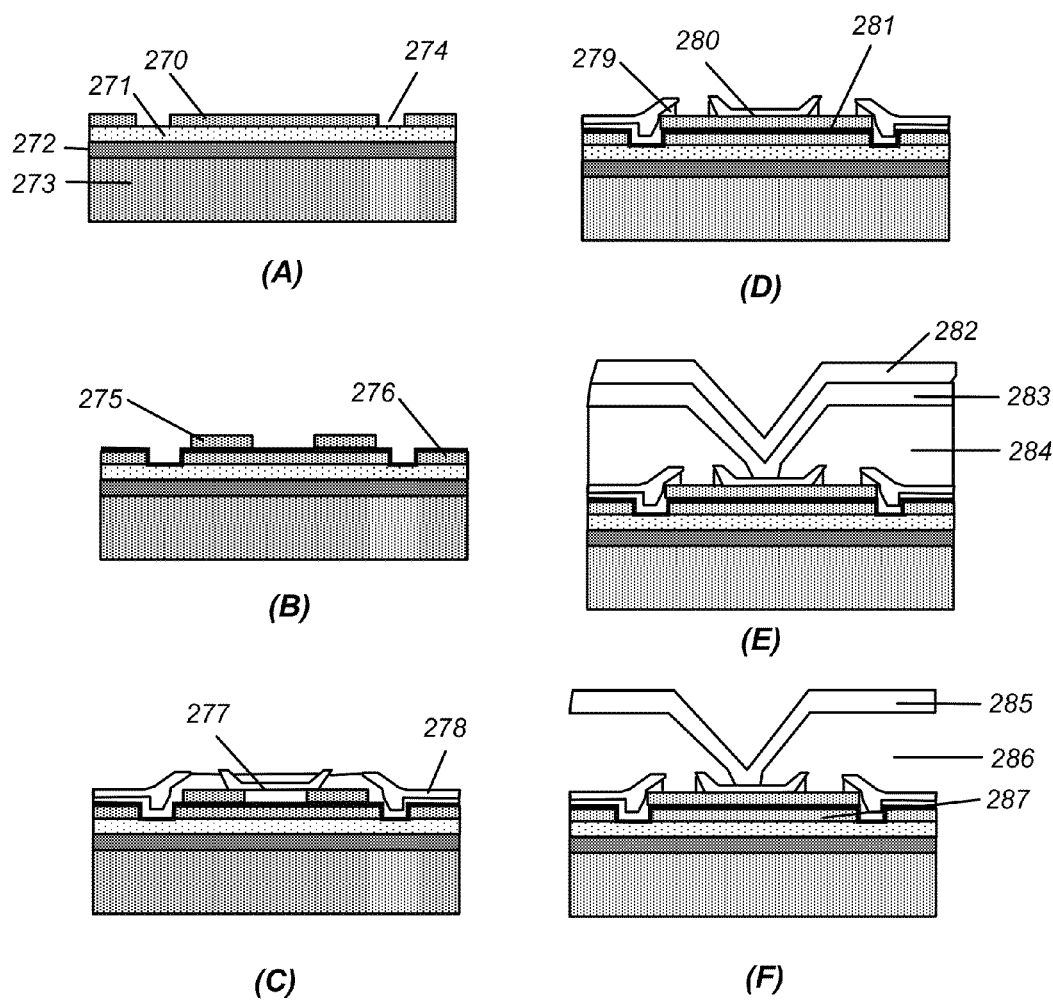
FIGS. 15A-15F are simplified schematic cross-sectional diagrams illustrating a process for fabricating a flipper type DNA ejection device similar to a digital micromirror device (DMD™)

FIGS. 14A-14 F are simplified schematic diagrams illustrating a DNA ejection device using a combination of a lateral electrostatic comb-drive actuator and a thermal bimetallic actuator. The actuator uses strips of 2 different metals with different coefficients of thermal expansion. One strip can be a resistance heater 250 the other can be made of silicon or polysilicon 251. When heat is generated in the dissimilar metals a shape change occurs in the cantilever causing it to move closer to the carrier. Starting in 253 and ending in 256 the thermal bimetallic cantilever is activated at the same time as the comb drive actuator propelling the comb forward to release DNA only in the "lanes" where the thermal bimetallic cantilevers are activated. As illustrated in FIGS. 14A-14F, the application of thermal energy produces changes in shape of the arm made of the two different materials. These shape changes result in bending of the structure, which then can be used to scrape the DNA off of the support. This effect can be used in conjunction with the comb drive so that although all the combs move, only certain DNA samples are ejected at locations where the structure changes shape.

FIGS. 15A-15F are simplified schematic cross-sectional diagrams illustrating a process for fabricating a flipper type DNA ejection device similar to a digital micromirror device (DMD™). The process begins on a completed SRAM address circuit board 273 (a form of non-volatile memory that uses a bi-stable latching circuitry). A thick oxide is deposited on top and then polished to ensure a completely planar surface for the flipper superstructure 272. Vias are made into this chemical mechanically polished oxide (not shown). Aluminum 271 is deposited on top of the oxide and spacers are deposited on top of the metal using spin coating and lithographic hardening 270. Spacervias-1 274 form metal support post as well as support for the addressing electrodes (shown more clearly in the next figure) after the yoke metal covers there sidewalls. These support post support the hinges.

After spacer-1 patterning 270 a thin metal layer is sputtered to form the hinges 276. Oxide hinge mask are then patterned 275, these act as an etch mask for the hinges later in the process. Next a thicker layer of aluminum is sputtered to form the yoke layer 278. This covers the hinge metal 276 and the oxide hinge mask 275. Another oxide mask is placed over the yoke 277 so that it does not erode during plasma metal etching. This metal etching step properly forms the hinge support post 279 and uncovers the hinge. The oxide yoke mask can then be removed.

Afterwards a mask is deposited over the yoke to form spacervia-2 which connects the flipper to the yoke. Then oxide patterning is done forming spacer-2 284, followed by deposition of an aluminum flipper layer 283 followed by another oxide flipper mask 282. The last step is to remove spacers 1 and 2 to form the air gaps 286 and 287 above and below the hinge to enable movement of the unencumbered flipper 285.

Figure 16:
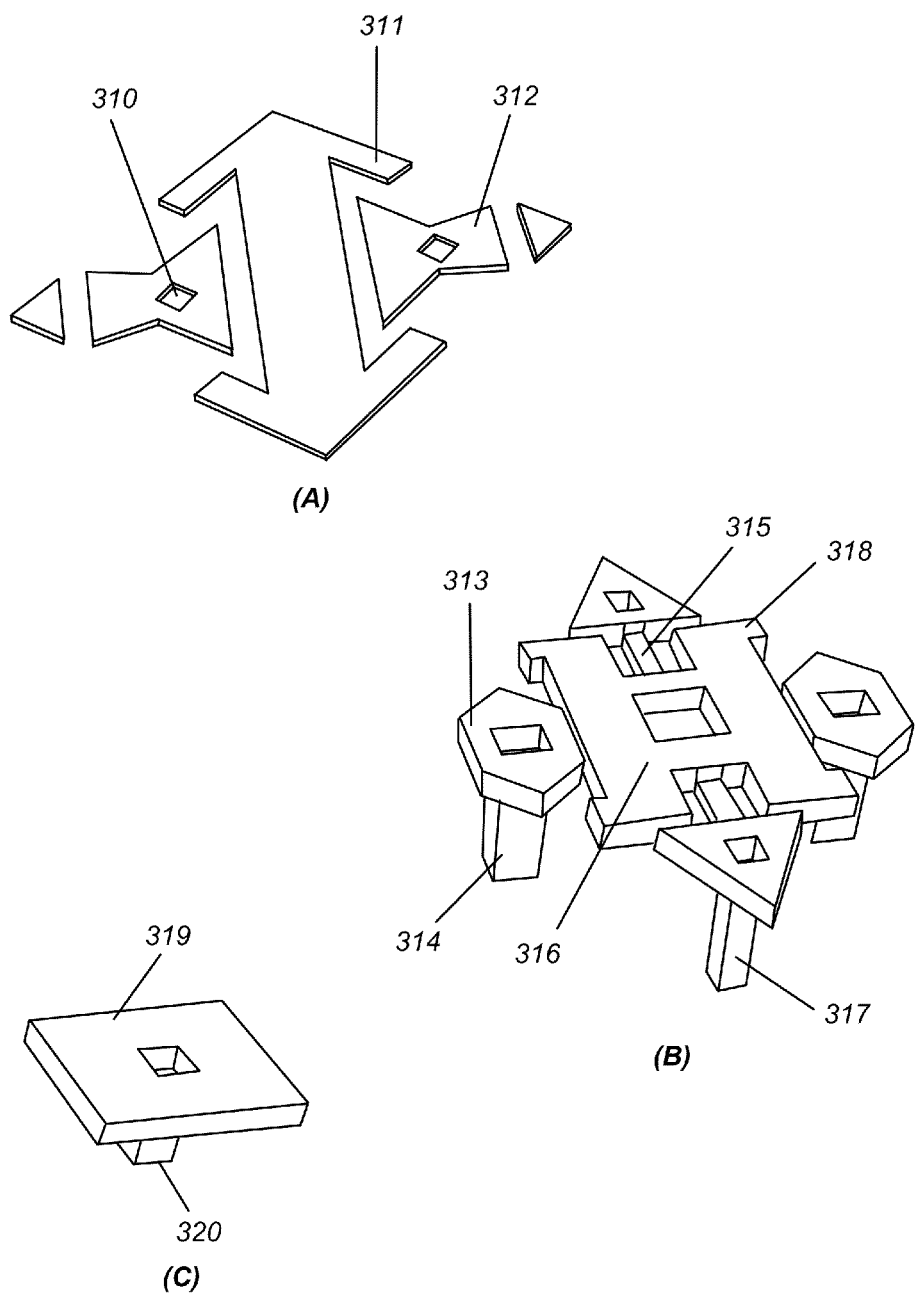
FIGS. 16A-16C are simplified schematic diagrams illustrating three-dimensional views of the various components of the flipper-type DNA ejection device fabricated using the process illustrated in FIGS. 15A-15F.

FIGS. 16A-16C are simplified schematic diagrams illustrating three-dimensional views of the various components of the flipper-type DNA ejection device fabricated using the process illustrated in FIGS. 15A-15F. The first inset shows the metal 3 covered SRAM 312 (271 in the previous 2D figure) with a via to the underlying circuitry 310. The landing area for the flipper ejector is also shown 311. The next inset shows a 3D view of the $2^{nd}$ layer. Addressable electrodes 313 rest on top of electrode support post 314, which link to vias in the SRAM layer. Torsion hinges, allowing for movement 315 connect the yoke 316 to the torsion hinge supports 317. 318 shows the yoke landing tip where it comes into contact with the 311 in the first insert of the figure. 319 shows the flipper structure where the carrier bound DNA is attached and the support post 320 that connects it to the yoke.

Figure 17:
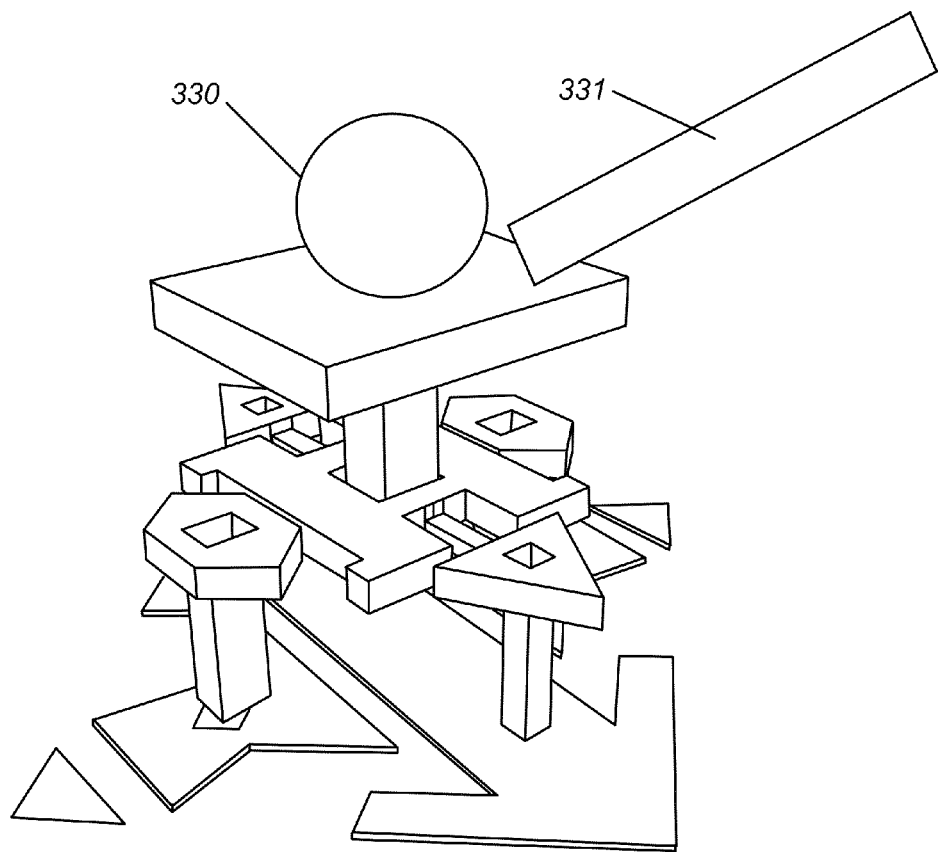
FIG. 17 is a simplified schematic diagram illustrating a composite three-dimensional view of the flipper-type DNA ejection device fabricated using the process illustrated in FIGS. 15A-15F.

FIG. 17 is a simplified schematic diagram illustrating a composite three-dimensional view of the flipper-type DNA ejection device fabricated using the process illustrated in FIGS. 15A-15F. The DNA ejection flipper is shown along with carrier bound DNA 330 on the surface 311. A simplified kicker 331 is also shown. The kicker can be a static object or it can be another flipper set at a different height so the flipper and kicker generate a greater combined force on the carrier bound DNA.

Figure 18:
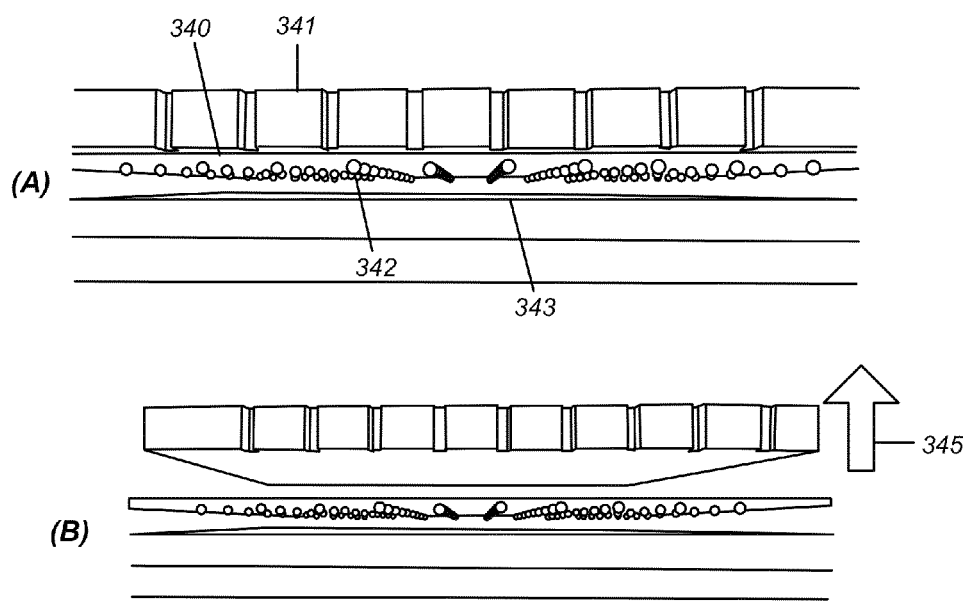
FIGS. 18A and 18B are simplified schematic diagrams illustrating the transfer of sequenced DNA from a sequencing substrate to an ejection device.

FIGS. 18A and 18B are simplified schematic diagrams illustrating the transfer of sequenced DNA from a sequencing substrate to an ejection device. The carrier bound DNA 342 ordered on a patterned flow cell 340 is transferred to a MEMS array 343. The removal 345 of a the backing magnet 341 allows the magnetic DNA bound carrier, in this case in bead format, to be released (not shown).

In some embodiments, DNA is sequences on a separate sequencing device. Then, the sequenced DNA is transferred to a device that is suitable for ejection of the DNA (an ejection device). In this embodiment, sequencing is performed on glass and then transferred onto an ejection device, for example, a digital micromirror device. This process will enable sequencing in a first environment (e.g., a wet environment) and ejection will be performed in a second environment (e.g., a dry environment).

Figure 19:
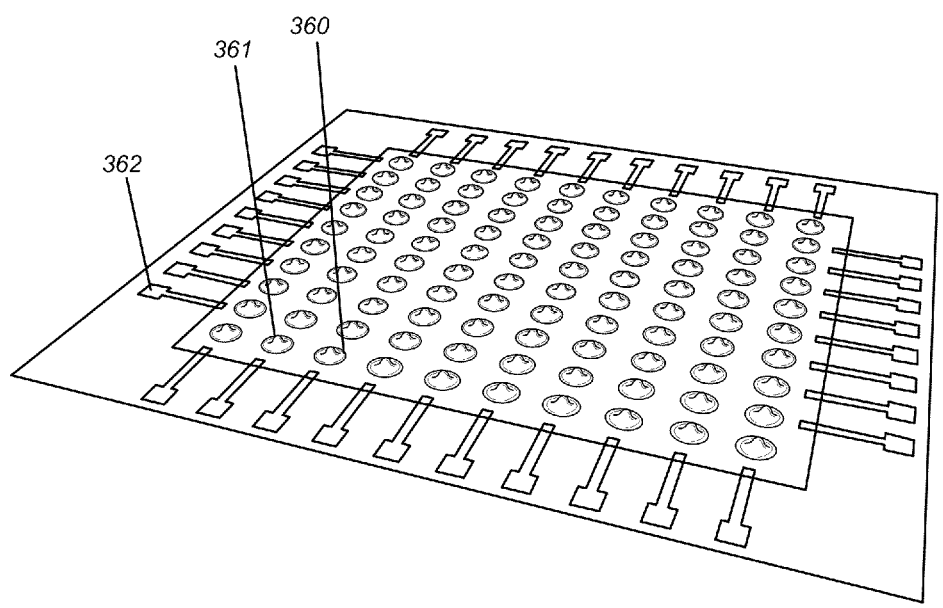
FIG. 19 is a simplified schematic diagram illustrating a fluidic based ejection system in which sequenced DNA is released via electrogenerated acid.

FIG. 19 is a simplified schematic diagram illustrating a fluidic based ejection system in which sequenced DNA is released via electrogenerated acid. The MEMS system uses a platinum anode 361 surrounded by a counter cathode 360 the same as is used in electrochemical DNA synthesis as shown in FIG. 3. In this system electrogenerated acid is used to release carrier bound DNA so that it can be recovered fluidicaly. Contact pads are also shown 362.

Figure 20:
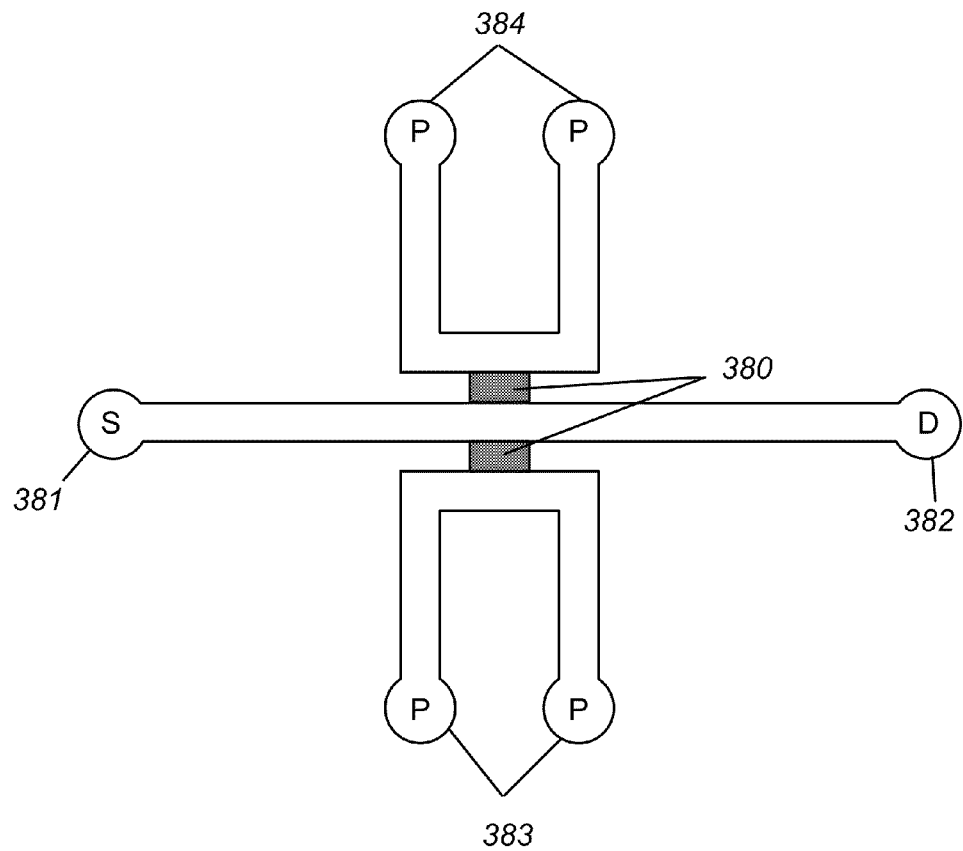
FIG. 20 is a simplified schematic diagram illustrating a electrokinetic DNA concentrator used to concentrate DNA for further amplification after release into a fluidic environment.

FIG. 20 is a simplified schematic diagram illustrating a electrokinetic DNA concentrator used to concentrate DNA for further amplification after release into a fluidic environment. The electrokinetic concentrator works based on principles of electrosmosis used to move the liquid and electrophoresis to trap the negatively charged DNA. P represents the reservoirs left and right, 384, 383 which are grounded to 0 V, cations are selectively extracted through the negatively charged hydrogel, and anions expelled from the area near the negatively charged hydrogel 380. As a result, an ion-depleted region develops between the two hydrogel plugs. Along the ion-depleted region, the electric resistance and corresponding electric field substantially increase. Therefore, electrophoretic force (EP) is locally strengthened at the ion-depletion region. Near the ion-depletion region, the direction of anion EP is the opposite of the EOF of the main channel, thus anions entering the ion-depleted region experience an enhanced EP that drives back toward the sample reservoir. Consequently, anions are stacked to the left of the ion-depletion boundary where the main channel flow rate and EP balances each other. To trap of the DNA oligonucleotides in a buffer mixture are flowed into the main channel (S-D) 381, 382. At this point 40 V at the sample reservoir (S), 5 V at the drain reservoir (D), and 0 V at the polymer reservoirs (P). If the DNA is fluorescently labeled, at time zero, before the voltage application, the fluorescence signal is very weak. However, a strong fluorescent signal will be detected at the left side of the ion-depleted region after the application of voltage. Using an electokinetic concentrator DNA can be rapidly and effectively concentrated using the digital micromirror fabricated charged nanoporous hydrogel system for concentration of DNA released from a sequencing chip into a microfluidic channel.

Referring to FIG. 20, the electrokinetic concentrator uses electroosmosis to move a liquid (e.g., water) containing the DNA and electrophoresis to concentrate the charged molecules. The liquid containing the charged molecules enters at the source S 381 and moves towards the drain D 382. Electrophoretic element 380 impedes the flow of the charged molecules as the liquid flows towards the drain, resulting in concentration of the charged molecules to the left of the electrophoretic element 380. Once sufficient concentration has been reached, the electrophoretic element can be disabled, enabling the concentrated solution of charged molecules to proceed toward the drain.

Figure 21:
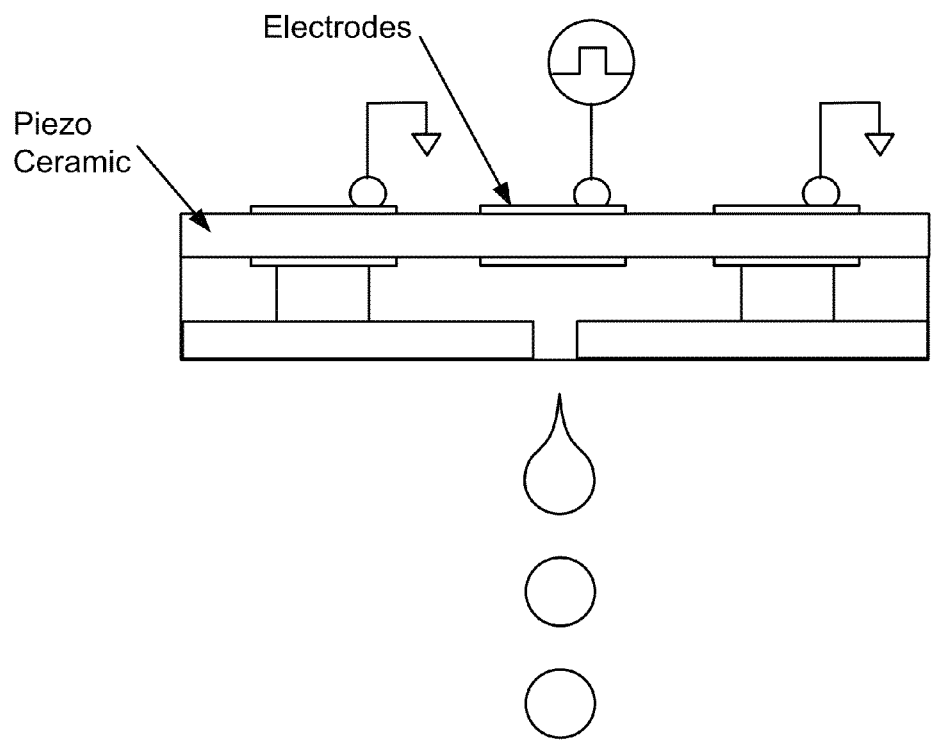
FIG. 21 is a simplified schematic diagram illustrating an jet-based DNA ejection system according to an embodiment of the present invention

FIG. 21 is a simplified schematic diagram illustrating an jet-based DNA ejection system according to an embodiment of the present invention. The system enables a method of retrieving sequence-verified deoxyribonucleic acid (DNA). The method includes positioning a sequence-verified DNA molecule on an jet-based system. The jet-based system comprises an orifice and the sequence-verified DNA molecule is positioned adjacent to the orifice. The method also includes causing a fluid to pass through the orifice, thereby ejecting the sequence-verified DNA molecule from the jet-based system. The jet-based system can include a thermal jet system or a piezoelectric jet system.

Figure 22:
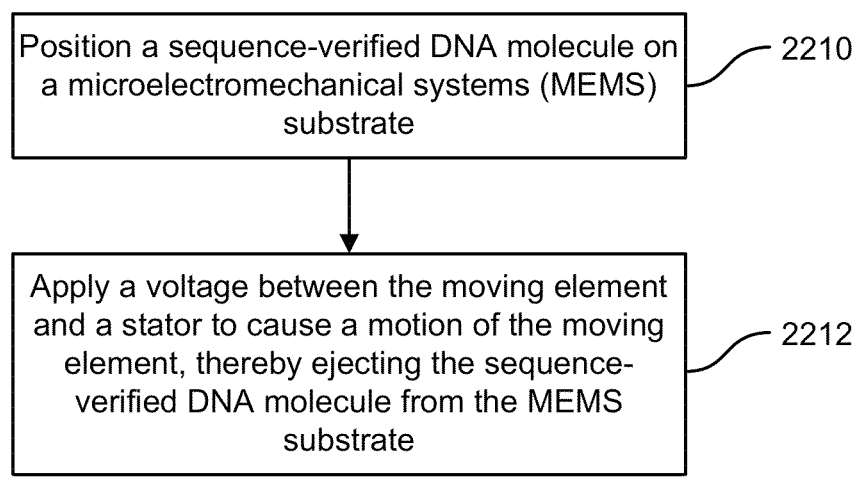
FIG. 22 is a simplified flowchart illustrating a method of retrieving sequence-verified deoxyribonucleic acid (DNA)

FIG. 22 is a simplified flowchart illustrating a method of retrieving sequence-verified deoxyribonucleic acid (DNA). The method includes positioning a sequence-verified DNA molecule on a microelectromechanical systems (MEMS) substrate (2210). The MEMS substrate includes an electrostatic actuator and the sequence-verified DNA molecule is positioned adjacent to a moving element. In an embodiment, the electrostatic actuator has a rotor and a stator. As an example, the moving element can include a rotor. In other embodiments, the electrostatic actuator is a comb-drive actuator and the motion of the rotor can be a lateral motion with respect to the stator. In a specific embodiment, the motion of the rotor is a transverse motion with respect to the stator. In some implementations, the rotor of the comb-drive actuator is attached to a flexible polymer. The electrostatic actuator can also be a parallel-plate type electrostatic actuator or a radial electrostatic actuator.

The method also includes applying a voltage between the moving element and a stator to cause a motion of the moving element, thereby ejecting the sequence-verified DNA molecule from the MEMS substrate (2212). In some embodiments, the MEMS substrate further includes an electrostatic kicker disposed adjacent to the sequence-verified DNA molecule. The method then includes concurrent to applying a voltage, activating the electrostatic kicker. The sequence-verified DNA molecule can be in an aqueous environment or a dry environment.

Positioning of the sequence-verified DNA molecule can include forming a sequence-verified DNA molecule on the MEMS substrate or transferring a sequence-verified DNA molecule onto the MEMS substrate depending on the embodiment. The sequence-verified DNA molecule can also be formed on a solid carrier such as a bead. In some implementations, the sequence-verified DNA molecule is separated from the MEMS substrate by a layer of sacrificial material.

It should be appreciated that the specific steps illustrated in FIG. 22 provide a particular method of retrieving sequence-verified deoxyribonucleic acid (DNA) according to an embodiment of the present invention. Other sequences of steps may also be performed according to alternative embodiments. For example, alternative embodiments of the present invention may perform the steps outlined above in a different order. Moreover, the individual steps illustrated in FIG. 22 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 23:
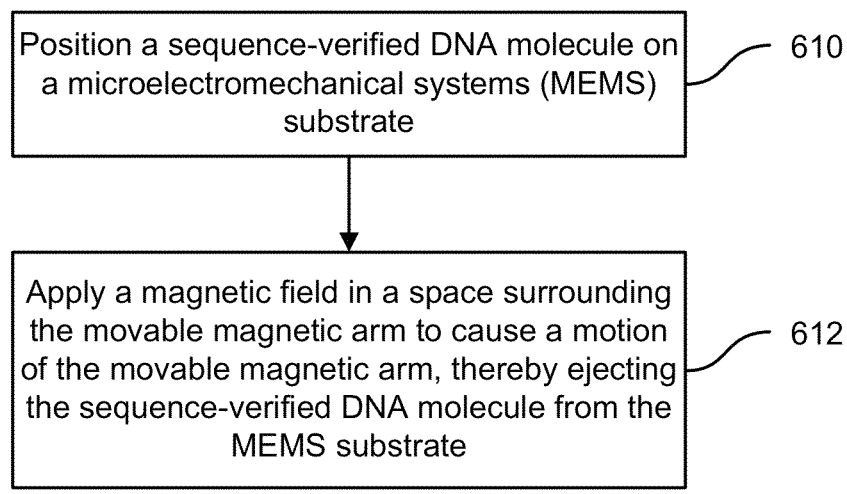
FIG. 23 is a simplified flowchart illustrating a method of retrieving sequence-verified DNA.

FIG. 23 is a simplified flowchart illustrating a method of retrieving sequence-verified DNA. The method includes positioning a sequence-verified DNA molecule (e.g., in an aqueous environment or a dry environment) on a microelectromechanical systems (MEMS) substrate (2310). The MEMS substrate includes a magnetic actuator having a movable magnetic arm and the sequence-verified DNA molecule is positioned adjacent to the movable magnetic arm. The motion of the movable magnetic arm can be a torsion motion with respect to an axis of the movable magnetic arm. Additionally, the movable magnetic arm can be a cantilever arm and the motion of the movable magnetic arm would be a deflective motion with respect to a base of the movable magnetic arm.

The method also includes applying a magnetic field in a space surrounding the movable magnetic arm to cause a motion of the movable magnetic arm, thereby ejecting the sequence-verified DNA molecule from the MEMS substrate (2312). Positioning the sequence-verified DNA molecule can include forming a sequence-verified DNA molecule on the MEMS substrate or transferring the sequence-verified DNA molecule onto the MEMS substrate.

In some embodiments, the sequence-verified DNA molecule can be formed on a solid carrier, for example, a bead. Additionally, the solid carrier can be ferromagnetic, paramagnetic, or superparamagnetic.

It should be appreciated that the specific steps illustrated in FIG. 23 provide a particular method of retrieving sequence-verified DNA according to an embodiment of the present invention. Other sequences of steps may also be performed according to alternative embodiments. For example, alternative embodiments of the present invention may perform the steps outlined above in a different order. Moreover, the individual steps illustrated in FIG. 23 may include multiple sub-steps that may be performed in various sequences as appropriate to the individual step. Furthermore, additional steps may be added or removed depending on the particular applications. One of ordinary skill in the art would recognize many variations, modifications, and alternatives.

It should be appreciated that the methods and systems described herein can be used in an interchangeable manner, with components and techniques utilized in one implementation also utilized in alternative implementations. One of ordinary skill in the art would recognize many variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of retrieving sequence-verified deoxyribonucleic acid comprising:
    positioning a sequence-verified deoxyribonucleic acid molecule on a microelectromechanical systems substrate, wherein the microelectromechanical systems substrate includes an electrostatic actuator having a stator, and wherein the sequence-verified deoxyribonucleic acid molecule is positioned adjacent to a moving element;
    applying a voltage between the moving element and the stator to cause a motion of the moving element;
    thereafter ejecting the sequence-verified deoxyribonucleic acid molecule from the microelectromechanical systems substrate in response to the applied voltage; and
    retrieving the deoxyribonucleic acid molecule.

2. The method of claim 1 wherein the electrostatic actuator has a rotor.

3. The method of claim 2 wherein the motion of the rotor is a lateral motion with respect to the stator.

4. The method of claim 1 wherein the moving element comprises a rotor.

5. The method of claim 1 wherein positioning a sequence-verified deoxyribonucleic acid molecule comprises forming the sequence-verified deoxyribonucleic acid molecule on the microelectromechanical systems substrate.

6. The method of claim 1 wherein the sequence-verified deoxyribonucleic acid molecule is separated from the microelectromechanical systems substrate by a layer of sacrificial material.

7. The method of claim 1 wherein the electrostatic actuator comprises a comb-drive actuator.

8. The method of claim 1 wherein the sequence-verified deoxyribonucleic acid molecule is in an aqueous environment.

9. The method of claim 2 wherein the motion of the rotor is a transverse motion with respect to the stator.

10. The method of claim 1 wherein positioning a sequence-verified deoxyribonucleic acid molecule comprises transferring the sequence-verified deoxyribonucleic acid molecule onto the microelectromechanical systems substrate.

11. The method of claim 1 wherein the sequence-verified deoxyribonucleic acid molecule is in a dry environment.

* * * * *